United States Patent
Duncan et al.

(10) Patent No.: US 12,053,578 B2
(45) Date of Patent: Aug. 6, 2024

(54) RESPIRATOR DESIGNED TO MITIGATE DEEP LUNG INFECTIONS

(71) Applicant: Texas Tech University System, Lubbock, TX (US)

(72) Inventors: Robert V. Duncan, Corpus Christi, TX (US); Annette L. Sobel, Corpus Christi, TX (US); Cuikun Lin, Lubbock, TX (US); Christopher Carty, Lubbock, TX (US); Robert Baca, Lubbock, TX (US); Moses Trevor Dardik, Andover, MA (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 17/911,249

(22) PCT Filed: Mar. 16, 2021

(86) PCT No.: PCT/US2021/022550
§ 371 (c)(1),
(2) Date: Sep. 13, 2022

(87) PCT Pub. No.: WO2021/188529
PCT Pub. Date: Sep. 23, 2021

(65) Prior Publication Data
US 2023/0100974 A1    Mar. 30, 2023

Related U.S. Application Data

(60) Provisional application No. 62/991,122, filed on Mar. 18, 2020, provisional application No. 62/990,224, filed on Mar. 16, 2020.

(51) Int. Cl.
*A61M 16/00*    (2006.01)
*A61M 16/10*    (2006.01)

(52) U.S. Cl.
CPC ...... *A61M 16/0009* (2014.02); *A61M 16/024* (2017.08); *A61M 16/109* (2014.02);
(Continued)

(58) Field of Classification Search
CPC ............ A61M 16/0009; A61M 16/024; A61M 16/0003; A61M 16/0006; A61M 2016/0039
See application file for complete search history.

(56) References Cited

U.S. PATENT DOCUMENTS

| 2005/0051174 A1 | 3/2005 | Emerson |
| 2006/0207602 A1 | 9/2006 | Kolobow et al. |

(Continued)

FOREIGN PATENT DOCUMENTS

WO    2011/042908 A1    4/2011

OTHER PUBLICATIONS

International Search Report and Written Opinion for PCT/US2021/022550 dated Jul. 28, 2021.
(Continued)

*Primary Examiner* — Margaret M Luarca
(74) *Attorney, Agent, or Firm* — Edwin S. Flores; Daniel J. Chalker; Chalker Flores, LLP

(57) ABSTRACT

The present invention includes an apparatus and method for breaking up mucus in a lung comprising: a chamber having an inlet and an outlet; a pressure oscillating unit in fluid communication with the chamber for supplying and vacuuming air into/out of the chamber, wherein the pressure oscillating unit creates ultrasound waves; a control unit for selecting a positive air pressure or a negative air pressure from the pressure oscillating unit, a fluid container in fluid communication with the chamber; a pressure sensor in fluid communication with the chamber; and an outlet connected to the chamber to send respiration gas to a patient, ultrasonic (Continued)

waves in the respiration gas are capable of breaking up mucus in the lung.

8 Claims, 4 Drawing Sheets

(52) U.S. Cl.
CPC ............... *A61M 2016/0027* (2013.01); *A61M 2205/502* (2013.01); *A61M 2230/435* (2013.01)

(56) References Cited

U.S. PATENT DOCUMENTS

| | | |
|---|---|---|
| 2009/0098015 A1 | 4/2009 | Bhardwaj |
| 2014/0150791 A1 | 6/2014 | Birnkrant et al. |
| 2014/0190481 A1* | 7/2014 | Jam ..................... A61M 16/024 128/205.24 |
| 2018/0085541 A1 | 3/2018 | Ye et al. |
| 2018/0243518 A1 | 8/2018 | Sing et al. |

OTHER PUBLICATIONS

Xu, Z., et al., "Pathological findings of COVID-19 associated with acute respiratory distress syndrome," Lancet Respir Med (2020), 8:420-422.

Partial Supplemental European Search Report, EP 21771670.3 dated May 5, 2024.

* cited by examiner

RESPIRATOR DESIGNED TO MITIGATE DEEP LUNG INFECTIONS

CROSS-REFERENCE TO RELATED APPLICATIONS

This application is the National Stage of International Application No. PCT/US2021/022550, filed on Mar. 16, 2021 claiming the priority to U.S. Provisional Application Ser. No. 62/990,224 filed Mar. 16, 2020 and U.S. Provisional Application Ser. No. 62/991,122 filed Mar. 18, 2020, the entire contents of which are incorporated herein by reference.

TECHNICAL FIELD OF THE INVENTION

The present invention relates in general to the field of respirators, and more particularly, to a new respirator designed to mitigate deep lung infections.

STATEMENT OF FEDERALLY FUNDED RESEARCH

None.

BACKGROUND OF THE INVENTION

Without limiting the scope of the invention, its background is described in connection with respiratory problems.

Certain potentially lethal human respiratory infections such as COVID-19 begin in the upper respiratory tract, much like the common cold, and become life-threatening if the infection spreads deeper into the lungs. Recent studies show that there was a large amount of mucus in the lungs of the deceased. White foam-like mucus was seen in the trachea, and jelly-like mucus was adhered to the bronchi of the right lung. The mucus was caused by an inflammatory response caused by virus. A large number of sticky secretions overflowed from the alveolar section. [1, 2]

What is needed is a novel device and method for treating and removing the large amount of mucus in the lungs, so that blood gas exchange may be established in the alveoli while avoiding the further transfer of micro-organisms and other pathogens to the lower lung.

SUMMARY OF THE INVENTION

In one embodiment, the present invention includes a respiratory device capable of breaking up mucus in a lung comprising: a chamber having an inlet and an outlet; a pressure oscillating unit in fluid communication with the chamber for supplying and vacuuming air into/out of the chamber, wherein the pressure oscillating unit creates ultrasound waves; a control unit for selecting a positive air pressure or a negative air pressure from the pressure oscillating unit, a fluid container in fluid communication with the chamber; a pressure sensor in fluid communication with the chamber; and an outlet connected to the chamber to send respiration gas to a patient, ultrasonic waves in the respiration gas are capable of breaking up mucus in the lung. In one aspect, device further comprises a sensor in communication with the outlet of the chamber that measures an air flow into and out of the patient during breathing. In another aspect, the chamber is defined further as a mask capable of a substantially hermetic seal with a patient. In another aspect, the device further comprises a port in fluid communication with the chamber wherein an aerosolized drug can be injected into the chamber via the port. In another aspect, the control unit adjusts an oxygen partial pressure, and an amount of an aerosolized drug cocktail that is mixed with air to form an inhalant that is delivered to the lung. In another aspect, the control unit adjusts the ultrasound waves into the outlet over a range of frequencies and intensities that are either set manually or set automatically through an automated system. In another aspect, the pressure oscillating unit generates a large amplitude, negative pressure swing to force rapid exhalation. In another aspect, the control unit adjusts one or more parameters selected from: a duration and a degree of overpressure and under-pressure applied during a patient's breathing sequence, a frequency of therapeutic bursts, a frequency and intensity of ultrasound levels, a ratio of oxygen partial pressure mixed with air, and a dose of aerosolized drug delivery that is added to the inhalant, wherein each can be adjusted (1) manually, (2) automatically with by a pre-programmed sequence, or (3) adaptively by a code segment that adjusts the one or more parameter to: increase a level of inhalant flow into and out of the lungs, to increase the $pO_2$ indication from the patient, or both. In another aspect, the positive pressure is less than 30 mm $H_2O$, the magnitude of the negative pressure is equal to or greater than −30 mm $H_2O$, or both, and wherein the negative pressure will be less than 30 cm of $H_2O$. In another aspect, the positive pressure is 5, 10, 15, 20, or 25 mm $H_2O$, the negative pressure is less than −5, −10, −15, −20, or −25 mm $H_2O$, or both. In another aspect, the controller operates in a normal mode that senses and adapts to a patient's normal respiration cycles, or that operates in a burst mode to break up the deep mucus on the alveoli. In another aspect, the device attaches to one or more intubation tubes and the controller applies one or more therapeutic sequences down an airway through the intubation tubes. In another aspect, the controller detects coughing and other indicators of respiratory reflex and distress. In another aspect, the controller detects sputum or other fluids, a valve opens to remove and contain the sputum or other secreted fluids. In another aspect, the sputum or other fluids comprise bacterial, fungal, or virus-laden expectorants. In another aspect, the controller is connected to a display or output that provides vital information selected from at least one of: natural breathing rates, inhalant flow rates a time profile while a patient breathes, a history efficacy of one or more parameters used in therapeutic bursts, a device that records a time history of a patient's vital statistics and medical record data. In another aspect, the device connected to a modified continuous positive airway pressure (CPAP) medical device to produce sudden swings to negative pressure, which are not provided by CPAP machines. In another aspect, the control unit adjusts one or more parameters for respiratory infections, generalized pneumonia conditions, pneumothorax conditions, drowning, or inhalation of high molecular-weight or toxic vapors. In another aspect, the chamber is connected to an intubation tube capable of direct connection to a lung damaged by a virus.

In another embodiment, the present invention includes a method of breaking up mucus in a lung the method comprising the steps of: providing a respiratory device comprising: a chamber having an inlet and an outlet; a pressure oscillating unit in fluid communication with the chamber for supplying and vacuuming air into the chamber, wherein the pressure oscillating unit creates ultrasound waves; a control unit for selecting a positive air pressure or a negative air pressure in rapid succession from the pressure oscillating unit, a fluid container in fluid communication with the chamber; a pressure sensor in fluid communication with the chamber; and an outlet connected to the chamber to send respiration gas to a patient, ultrasonic waves in the respiration gas are capable of breaking up mucus in the lung; and applying a fluid into the lung that comprises ultrasonic waves that are oscillated to break-up a mucus mass in the lungs. In one aspect, the method of claim 20, further comprising providing a sensor in communication with the outlet of the chamber that measures an air flow into and out of the patient during breathing. In another aspect, the chamber is defined further as a mask capable of a substantially hermetic seal with a patient. In another aspect, the method further comprises providing a port in fluid communication with the chamber wherein an aerosolized drug can be injected into the chamber via the port. In another aspect, the control unit adjusts an oxygen partial pressure, and an amount of an aerosolized drug cocktail that is mixed with air to form an inhalant that is delivered to the lung. In another aspect, the control unit adjusts the ultrasound waves into the outlet over a range of frequencies and intensities that are either set manually or set automatically through an automated system. In another aspect, the control unit adjusts one or more parameters selected from: a duration and a degree of overpressure and under-pressure applied during a patient's breathing sequence, a frequency of therapeutic bursts, a frequency and intensity of ultrasound levels, a ratio of oxygen partial pressure mixed with air, and a dose of aerosolized drug delivery that is added to the inhalant, wherein each can be adjusted (1) manually, (2) automatically with by a pre-programmed sequence, or (3) adaptively by a code segment that adjusts the one or more parameter to: increase a level of inhalant flow into and out of the lungs, to increase the $pO_2$ indication from the patient, or both. In another aspect, the positive pressure is less than 30 mm $H_2O$, the negative pressure is equal to or greater than −30 mm $H_2O$, or both, and wherein the negative pressure will be less than 30 cm of $H_2O$. In another aspect, the positive pressure is 5, 10, 15, 20, or 25 mm $H_2O$, the negative pressure is less than −5, −10, −15, −20, or −25 mm $H_2O$, or both. In another aspect, the controller operates in a normal mode that senses and adapts to a patient's normal respiration cycles, or that operates in a burst mode to break up the deep mucus on the alveoli. In another aspect, the device attaches to one or more intubation tubes and the controller applies one or more therapeutic sequences down an airway through the intubation tubes. In another aspect, the controller detects coughing and other indicators of respiratory reflex and distress. In another aspect, the when the controller detects sputum or other fluids, a valve opens to remove and contain the sputum or other fluids. In another aspect, the sputum or other fluids comprise bacterial, fungal, or virus-laden expectorants. In another aspect, the controller is connected to a display or output that provides vital information selected from at least one of: natural breathing rates, inhalant flow rates a time profile while a patient breathes, a history efficacy of one or more parameters used in therapeutic bursts, a device that records a time history of a patient's vital statistics and medical record data. In another aspect, the device connected to a modified continuous positive airway pressure (CPAP) medical device that further delivers or creates a negative pressure during exhalation. In another aspect, the control unit adjusts one or more parameters for respiratory infections, generalized pneumonia conditions, pneumothorax conditions, drowning, or inhalation of high molecular-weight or toxic vapors. In another aspect, the chamber to an intubation tube capable of direct connection to a lung damaged by a virus. In another aspect, the method further comprises generating a large amplitude, negative pressure swing to force rapid exhalation with the pressure oscillating unit.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
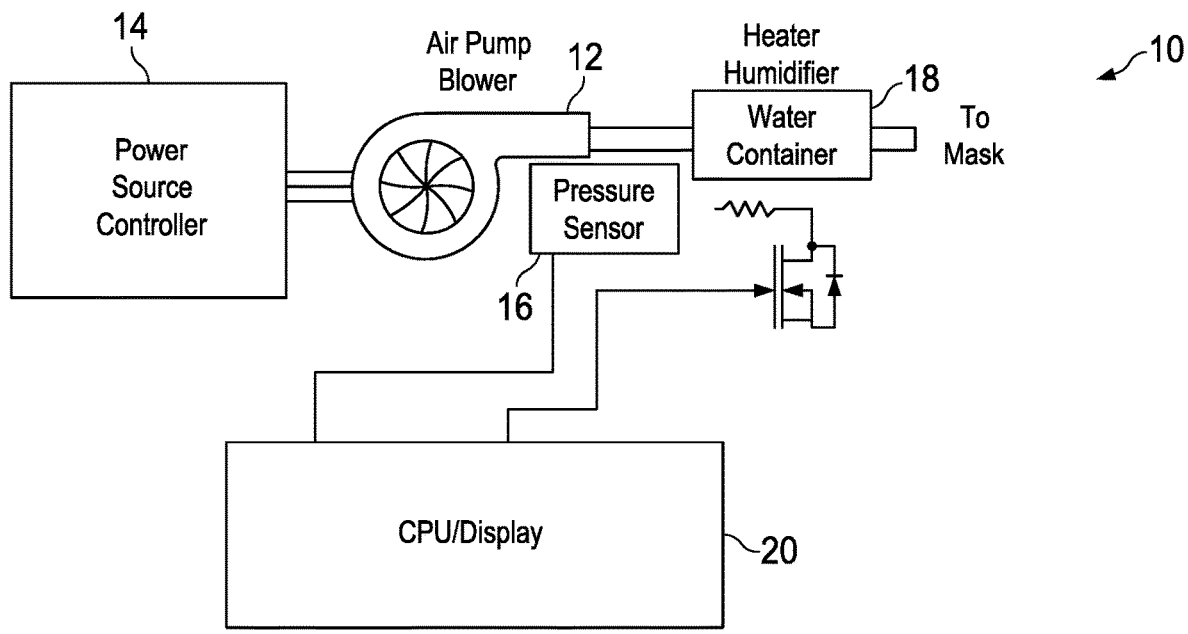
FIG. 1 shows a schematic diagram of a conventional continuous positive airway pressure (CPAP) device.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not limit the invention, except as outlined in the claims.

The present invention recognized the need to deal with fluid secretions of pneumonia, which are concentrated in the alveoli, resulting in the function of alveoli being greatly reduced and causing hypoxia. Unfortunately, conventional respirators typically only apply over-pressure at levels of about 30 cm of $H_2O$, to force air and oxygen into the lungs and small airways, followed by a pressure reduction to near ambient levels to permit the patient to exhale. This is problematic, since it actively provides a forcing function that migrates the infection from the upper respiratory tract into the bronchioles and alveoli in the lungs, where there is a much higher likelihood of morbidity or mortality. This medical concern has been confirmed in recent medical studies in the Wuhan region of China, where the current COVID-19 pandemic started.

Conventional respirators typically apply a large over-pressure to inflate the lungs as the patient inhales, and then relax this over pressure to near ambient conditions to permit the patient to exhale. The subject invention reverses this process: this new respirator applies a large negative pressure to assist the patient to exhale rapidly, and then relaxes this negative pressure to near ambient pressure to permit the patient to inhale. In that case of low paO$_2$ and demonstrated lung flow volume, or when the patient requires modest over-pressure to inhale, this new respirator may go to modest over pressures, and/or increase the oxygen partial pressure in the inhalant, in an attempt to raise the blood paO$_2$, but the exhalation is always intensified through the application of a large, negative pressure at the patient's face mask in order to move mucus, particulate, and micro-organisms into the upper respiratory tract and head, where these contaminants may be subsequently expectorated. Conventional respirators instead move these contaminants down to the lower respiratory tract, where they produce much more severe and potentially life-threatening lung infections, plugging the patient's critical gas exchange through the alveoli. This negative pressure actively assists the body's peristaltic motion of the cilia that attempt to move such impurities out of the lungs and bronchi, toward the upper respiratory tract for expectoration. The positive pressure application of conventional respirators works against this natural process of the body to clear the airways and preserve oxygenation.

The present invention creates a much larger negative pressure gradient as the patient exhales, in order to remove mucus, particulate, and micro-organisms from the lungs and bronchi. Existing regulators apply a positive gradient to inflate the lungs during inhalation, which accelerates these contaminants deeper into the respiratory tract, and into the bronchi and the lungs. The subject invention applies only ambient pressure (no positive pressure), or only very modest positive pressure as the patient begins to recover, greatly reducing this adverse effect from conventional respirators. If the patient is anesthetized, the device will provide a modest over-pressure, typically of about 7 cm of H$_2$O, in order to inflate the lungs slowly with the inhalant. The present invention applies a large negative pressure, typically in excess of −30 cm of H$_2$O, to assist the patient in exhalation, which works actively to assist the patient in removing these impurities from the lower portions of the respiratory tract (alveoli, and bronchioles).

The present invention includes a new design for a respirator that provides only modest overpressure of an oxygen-rich mixture with air, which can be supplemented with aerosolized medication to treat the respiratory infection. Then, instead of relaxing to ambient pressure to allow the patient to exhale, the subject invention actively applies a negative pressure below ambient in order to force exhalation. This provides a forcing function that assists the patient's respiratory physiology as it migrates the infected sputum and mucous from the lower, smaller airways into the upper respiratory tract, such as the trachea and mouth, where these infected fluids and solids may be naturally expectorated and/or suctioned out of the patient. Also, while under negative pressure, an oscillation in pressure can be applied to help loosen the mucus from the respiratory tree and small airways.

In addition, the subject invention permits integration with commercially-available intubation tube devices that may be used in concert with the improved respirator of the present invention to achieve fluid removal during the negative pressure phase, and the introduction of oxygen-enriched air with an optional drug aerosol during the modest, positive pressure phase. This cyclic process of negative pressure and oscillations to remove fluids, followed by modest positive pressure delivery of oxygen-rich air and medication, may be synchronized to the pressure cycles of the respirator, or operated independently of the respirator at the discretion of the medical care provider. Importantly, the present invention can be mass produced as a standalone, and even disposable device, or may be produced as a kit that is adapted for use with commercially-available intubation tube devices, thereby providing a surge of devices for hospitals that already have standard ventilators and/or intubation devices. Further, as medical care staff is already familiar with current respirators and intubation devices, minimal (or even no) training is required to operate the device of the present invention.

Medical resources, such as hospital beds, emergency room and intensive care access, and access to respirators, often become in critical short supply during a pandemic, and during other mass-casualty events. For example, the United States currently has just under one million hospital beds, which can accommodate only about 0.3% of the population. Of greater concern is the number of intensive care beds and respirators that are available and accessible in more remote, rural areas, which is currently only about 50,000, which could accommodate only about 0.01% of the population of the United States. A pandemic can easily result in much greater demand for these life-saving medical facilities than the current supply can provide. Hence, the present invention is designed to also be used with mass-produced commercially available components, such as the air pumps that are in use within millions of Continuous Positive Airway Pressure (CPAP) machines that are prescribed across the population and readily available to the more vulnerable portion of the population, including those over age 60 and with chronic lung disease and other comorbidities such as hypertension and diabetes, with the addition of a source of vacuum to provide significant negative pressure. The intubation option for the subject invention utilizes commercially available technology, such as endotracheal tubes or laryngeal mask airways (LMAs). This intubation option, however, is unlikely to be fully automated using existing devices, and will require the intervention of an emergency medical technician (EMT) paramedic or a trained medical professional. Once installed in this manner, an intubation tube may be brought into synchronous operation with this improved respirator design. This ready supply of mass-produced, commercially available components will permit original equipment manufacturers to scale up production to levels that approach capacity to meet the medical demand in response to a pandemic resulting in respiratory infection, morbidity and mortality.

The new respirator of the present invention features various modes of operation: the device will detect and measure normal respiration, including air flow and blood pO$_2$ concentrations, to establish an efficacy baseline before and after each therapeutic session. These therapeutic sessions will include cycles where the device will permit the patient to inhale at or only modestly above ambient pressure, followed by rapid forced exhale by establishing a large, negative pressure once the inhalation is complete. Causing the rapid forced exhale using a large, negative pressure once the inhalation is complete assures that the pressure differentials and subsequent inhalant flow rate into the lungs is small and progresses for a lengthy time (typically 2 to 3 seconds) during the inhalation half-cycle. Then, suddenly, large negative pressure (equal to or greater than −30 cm$^2$ of H$_2$O) is established to cause the patient to exhale very rapidly, typically within a second, or only slightly longer than that. In this way, a much larger and more impulsive flow of inhalant occurs out of the lungs, compared to the rate of inhalation. This larger and more impulsive flow of inhalant is the opposite of standard respirators that rapidly fill the lungs with inhalant by applying a large positive over-pressure during inhalation, and then relaxing to near ambient pressures to permit the patient to exhale slowly. The present invention provides the asymmetry that moves mucus and other obstructions of the alveoli up into the higher parts of the respiratory tract, instead of driving them downward toward the lungs, as conventional respirators would do. Throughout this process, ultrasound is used at the care giver's discretion at a frequency that presents a node structure similar to the size of the alveoli. The forced breathing, from near ambient pressure to inhale, to large negative pressure to assist in a very rapid exhale. The episodic bursting is when the near-ambient pressure for inhalation is followed by sudden negative pressure to force exhalation, with rapid repetition of this partial inhalation/exhalation cycle at a ramped frequency of up to five hertz. The ultrasound can be applied in a ramped frequency to span the ultrasound wavelength over the size of the alveoli and at an amplitude just under the threshold that would create shear damage to the lung tissue. Following the therapeutic treatments, the system goes back to measure the natural respiration rate, flow, etc.

Thus, the present invention provides a much safer and more effective respirator for all patients who require breathing assistance. Thus, in addition to critical care of COVID-19 patients who are severely ill, the present invention also finds therapeutic use with a wide-range of patients and applications, since it can be used to improve the health outcomes for mildly infected individuals who do not want the infection to spread to the lower lungs, and for patients undergoing surgery when they are on a respirator due to their anesthesia. This negative pressure will even advance the health of patients on CPAP machines (which only provide positive pressure), however in this modality, a substantial positive pressure would be necessary to prevent hypoxia during sleep that results the closure of the epiglottis without positive pressure during sleep. The present invention requires a larger negative pressure during exhalation to help migrate deep lung impurities and draw microorganisms out of the lungs and bronchi toward the head, where they may be expectorated by the patient. Finally, the subject invention may be used with patients who are on respiration in order to recover from severe lower respiratory infections, such as SARS, MERS, SARS-CoV2, pneumonia, etc.

The physical forcing function that is inadvertently applied by conventional respirators is exacerbated as the particulate size becomes smaller, and is much more substantial on the scale of the physical size of the alveoli (about 0.02 cm) and micro-organisms (about 0.0001 to 0.00001 cm). This is true because the mass of small particles is proportional to the volume of the particle, that scales with size as $r^3$. The force on the particle, however, is proportional to the applied pressure difference multiplied by the particle's cross-sectional area, and hence scales as $r^2$. Hence, the acceleration of the particle, which is equal to the net force of on the particle divided by its mass (Newton's Second Law), scales as $1/r$. Hence, much smaller particles, such as mucus plugs between and over the alveoli, and micro-organisms, are accelerated to a much greater degree than larger particles when subjected to the same pressure gradient. In the case of conventional respirators, this pressure gradient accelerates the small particles and micro-organisms much deeper into the lungs, compounding the life-threatening medical severity of conditions, such as deep-lung infections by SARS-CoV2 and other viruses that produce thick, sticky mucus that blocks gas exchange at the alveoli. The subject invention is a respirator that applies a negative pressure gradient to assist the patient to exhale, which accelerates these small mucus particles and micro-organisms in the opposite direction, out of the lower respiratory tract and lungs, toward the upper respiratory tract where they may be expectorated by the patient, or removed by suction at the patient's face-fitting mask. This huge health advantage of the subject invention is advantageous both in preventing lung and bronchi infections in generally healthy patients, and in re-establishing an airway in critically ill patients suffering from hypoxia that results from deep lung infections that block gas exchange directly at the alveoli. Given this medical advantage across-the-board, a major health advantage is obtained by using negative pressures to assist exhalation, relating to near ambient pressures to modest overpressure to permit inhalation, whenever a patient requires assistance in breathing.

The present invention can also be used to deliver medicaments into the intermediate and deep lung. Examples of medicaments include one or more anti-inflammatory compounds, vaccines, natural steroids, synthetic steroids, bronchodilators, vasodilators, naturopathic medicines, homeopathic medicines, antihistamines, antibiotics, anti-viral agents, anti-fungal agents, mucus production inhibitors, anti-tussive agents, anti-allergic agents, cough medications, tranquilizers, anesthetics, adrenergic receptor agonists, adrenergic receptor antagonists, beta-agonists, and/or beta-blockers, or gases such as nitrous oxide, oxygen, and air.

FIG. 1 shows a schematic diagram of a conventional continuous positive airway pressure (CPAP) device 10 of the prior art that includes a blower 12 under control of a controller and power-source 14, which provides a gradual increase and decrease in positive pressure, as measured by a pressure sensor 16, which blower 12 is connected to a water container 18 to humidify the air, under the control of a central processing unit (CPU) 20, which may include a display and user controls. CPAP machines do not provide for negative pressure.

Example 1. New Respirator to Mitigate Deep Lung Infections

Standard respirators go to an over-pressure of about 30 cm of $H_2O$ of a mixture of (oxygen/air/aerosolized-medication) to force the patient to inhale, and then relax to near ambient pressure conditions to permit the patient to exhale. Unfortunately, with COVID-19 disease (and similar respiratory infects of the lungs), this sequence simply drives the infection deeper into the lungs, compounding the disease's lethality. The thick, sticky mucus that the body produces in response to this virus physically blocks $O_2/CO_2$ gas exchange at the alveoli in severely infected patients. The only hope for the survival of these patients is in breaking up this thick, sticky mucus that has developed deeply in the lungs to provide better gas exchange at the alveoli. Eventually the patient's immune system will develop its own defenses against this virus. The present invention breaks up this thick, sticky mucus and establishes adequate gas exchange deep in the lungs, until the patient's own immune system can defeat the virus. The device of the present invention also provides a new concept and modality to treating any deep lung condition where simply applying over-pressure may further limit gas exchange at the alveoli, thereby compounding the severity of the patient's condition. These include generalized pneumonia conditions from any origin, certain pneumothorax conditions, and recovery from drowning or the inhalation of high molecular-weight or toxic vapors.

The device of the present invention used a much more modest over-pressure, typically from ambient pressure to 10 cm of $H_2O$, as the patient more slowly inhales, and then go to an under-pressure of about −10 to −30 cm of $H_2O$ to force a much more rapid exhalation. Like current CPAP machines, the pump will adapt to, and in this magnification measure, the natural period of exhale/inhale duration of the patient. During this process, the flow of air on each inhalation and exhalation will be measured, along with the patient's $pO_2$ level in the blood, and changes in this flow rate and $pO_2$ data will be used as an indicator of the effectiveness of the therapeutic bursts, as described below. The present invention provides an adaptive platform for using the pressure sequence to physically break up the dense, thick mucus, and a delivery mechanism for aerosolized medications to assist in breaking up this deep mucus, and to deliver anti-viral medications to destroy coronaviruses, such as MERS, SARS, SARS-CoV2 virus, rhinoviruses, and influenza viruses. It can also be used with bacterial and/or fungal infections. The operational parameters of the device of the present invention, such as the duration and degree of over-pressure and under-pressure, frequency of therapeutic bursts, frequency and intensity of ultrasound levels, ratio of oxygen partial pressure mixed with air, and the dose of aerosolized drug delivery that is added to the inhalant, may all be adjusted by either the care provider manually, or by an automated sequence within the device, to optimize the flow of the inhalant into and out of the lungs on each breath, and to increase the $paO_2$.

In operation, isolated bursts of a few seconds in duration will occur, consisting of the same modest over-pressure during inhalation and larger, negative pressure to force strong exhalation, but with a much faster frequency than the default, natural breathing frequency than that described above. This therapy will extend from the natural respiratory frequency of the patient to frequencies ranging up to about five times per second. An ultrasound transducer will also produce a pressure swing at a ultrasonic ramped frequency that varies throughout this process, corresponding to a wavelength that ranges from 0.02 to 0.04 millimeters, which is the typical size variation of the patient's alveoli. The intend of this rapid ultrasound variation is to break up the thick mucus deposit on the lung's alveoli, while the rapid pressure swings from over-to-under pressure is designed to assist the patient's cilia at their natural frequency as they attempt to clear the disrupted mucus from the respiratory tree towards the trachea and head. After each burst, the pressure swings will return to the adaptive, natural respiration frequency of the patient, and the flow rates during inhalation and exhalation will be once again measured, and the therapeutic approach will be evaluated through a comparison to the flow rates obtained previously. All of the parameters of this therapy, as listed above, may be varied in an attempt to improve lung airflow during respiration, and these optimal parameters can be adjusted manually, automatically, or as part of pre-set parameters that are updated to optimize the treatment.

Figure 2:
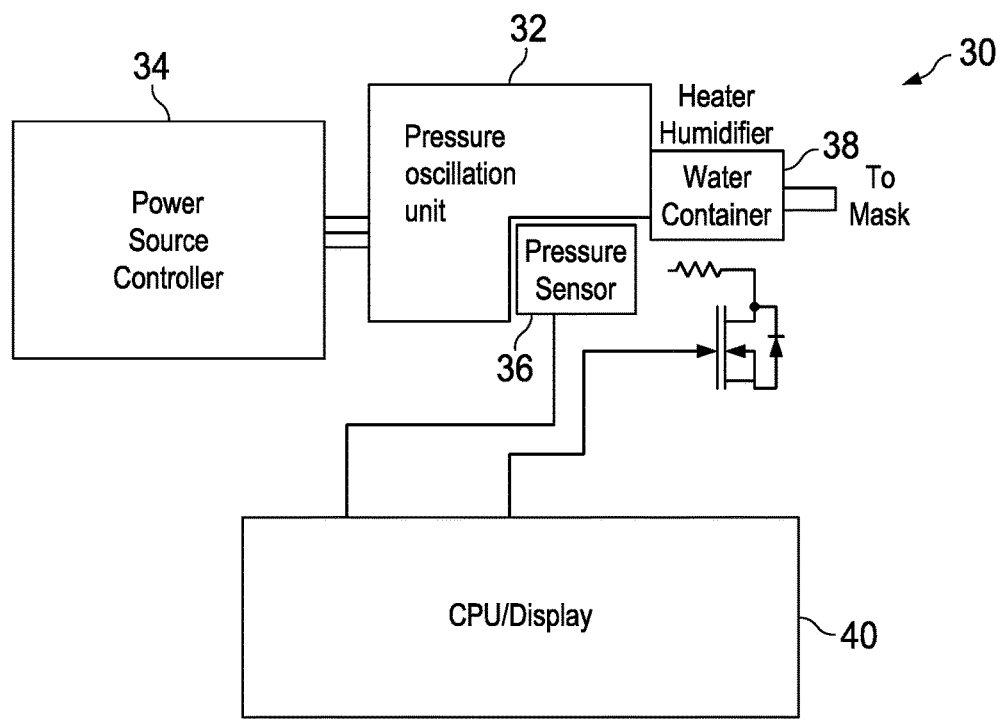
FIG. 2 shows a schematic diagram of the present invention in which a pressure oscillating unit is connected directly to a mask to provide a much larger and more impulsive flow of inhalant out of the lungs, compared to the rate of inhalation.

FIG. 2 shows a schematic diagram of the device 30 present invention in which a pressure oscillating unit 32 is connected directly to a mask to provide a much larger and more impulsive flow of inhalant out of the lungs, compared to the rate of inhalation. Unlike the blower used in the prior art, the present invention uses a pressure oscillating unit 32 that is used to cycle a fluid (such as air and/or other gases such as $O_2$) in the device to permit the patient to inhale at or only modestly above ambient pressure, followed by rapid forced exhale by establishing a large, negative pressure once the inhalation is complete, thereby helping cause the break-up of mucus and/or other secretions. The pressure oscillating unit 32 under control of a controller and power-source 34, which provides a gradual increase in positive pressure, followed by a more abrupt decrease in pressure to form a partial vacuum in the subject invention, as measured by a pressure sensor 36, and the pressure oscillating unit 32 is connected to a water container 38 to humidify the air, under the control of a central processing unit (CPU) 40, which may include a display and user controls.

Figure 3:
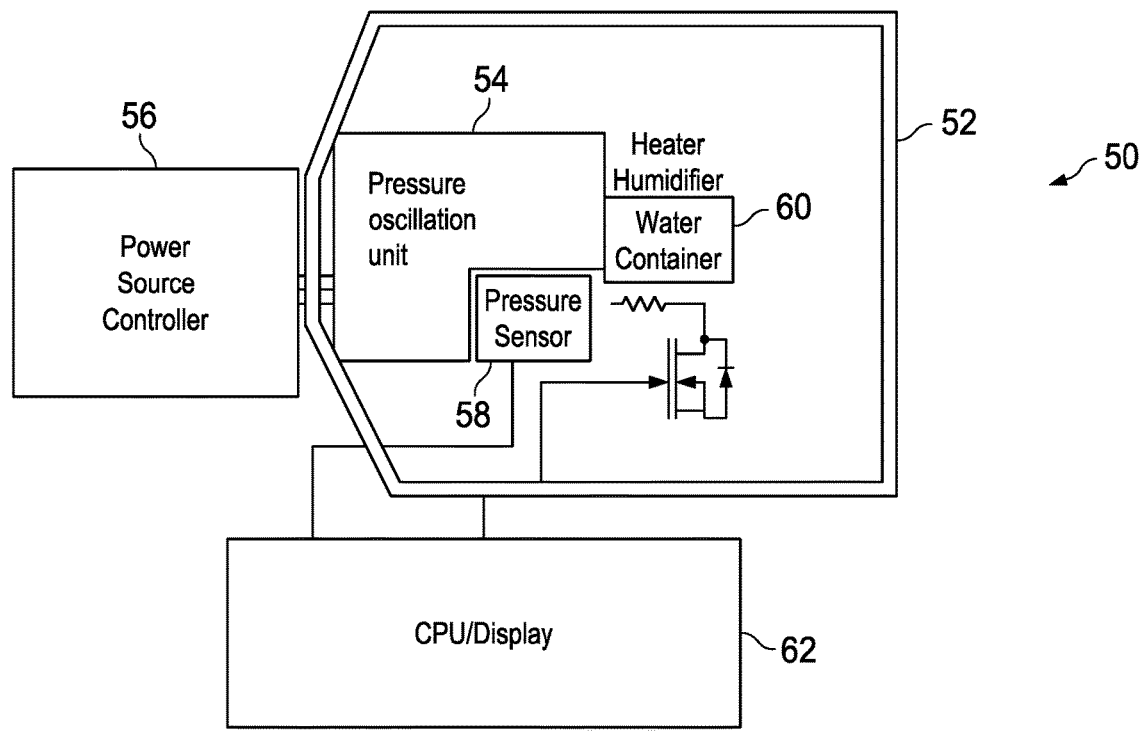
FIG. 3 shows a schematic diagram of the present invention in which a pressure oscillating unit is adjacent to, or integral with, a mask.

FIG. 3 shows a schematic diagram of another device 50 the present invention in which a pressure oscillating unit 54 is adjacent to, or integral with, a mask 52 to provide a much larger and more impulsive flow of inhalant out of the lungs, compared to the rate of inhalation. Generally, the mask will be selected to form a substantially hermetic seal between the mask 52 and a user. The pressure oscillating unit 54 that is used to cycle a fluid (such as air and/or other gases such as $O_2$) called the inhalant in the device to permit the patient to inhale at or only modestly above ambient pressure, followed by rapid forced exhale by establishing a large, negative pressure once the inhalation is complete, thereby helping cause the break-up of mucus and/or other secretions. The pressure oscillating unit 54 under control of a controller and power-source 56, which provides a gradual increase in positive pressure, followed by a decrease in pressure to form a partial vacuum, as measured by a pressure sensor 58, and the pressure oscillating unit 54 is connected to a water container 60 to humidify the air, under the control of a central processing unit (CPU) 62, which may include a display and user controls.

Figure 4:
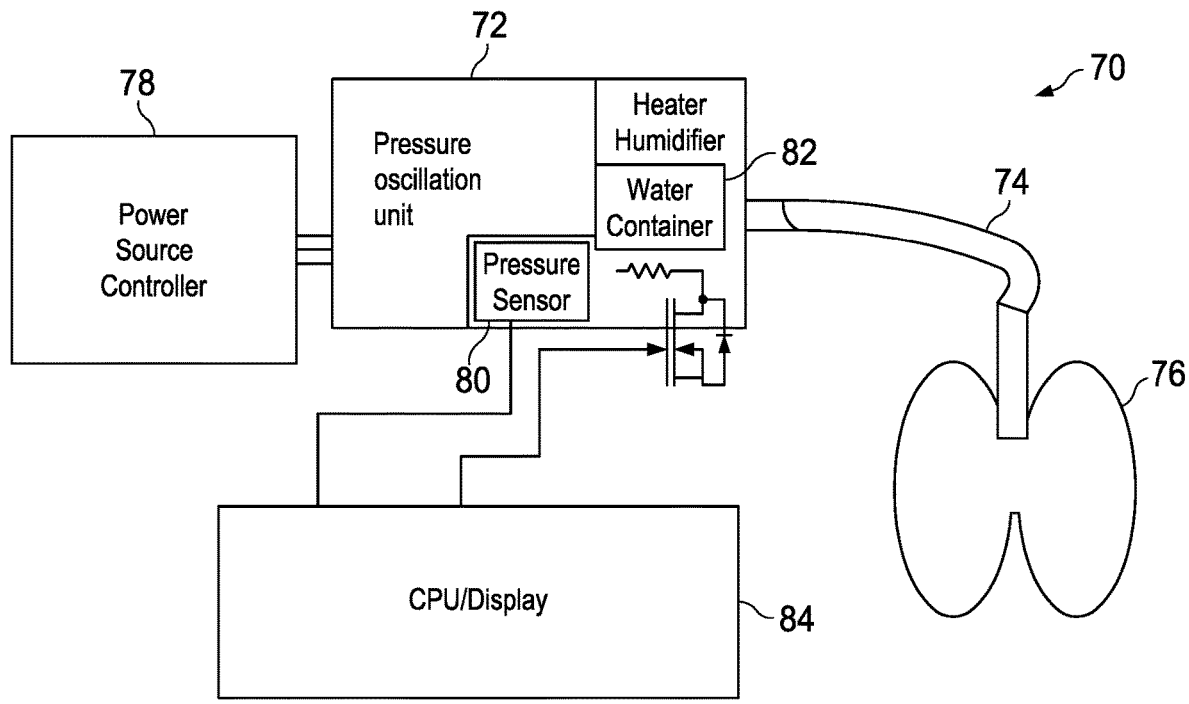
FIG. 4 shows a schematic diagram of the present invention in which a pressure oscillating unit is connected via an intubation tube to one or both lungs to deliver directed treatment to the intermediate and/or deep lung.

FIG. 4 shows a schematic diagram of the device 70 of the present invention in which a pressure oscillating unit 72 is connected via an intubation tube 74 to one or both lungs 76 to deliver directed treatment to the intermediate and/or deep lung. The pressure oscillating unit 72 provides a much larger and more impulsive flow of inhalant out of the lungs, compared to the rate of inhalation. The pressure oscillating unit 72 that is used to cycle a fluid (such as air and/or other gases such as $O_2$) called the inhalant in the device to permit the patient to inhale at or only modestly above ambient pressure, followed by rapid forced exhale by establishing a larger, negative pressure once the inhalation is complete, thereby helping create the break-up of mucus and/or other secretions. The pressure oscillating unit 72 under control of a controller and power-source 78, which provides a gradual increase in positive pressure, followed by a decrease in pressure to form a partial vacuum, as measured by a pressure sensor 80, and the pressure oscillating unit 72 is connected to a water container 82 to humidify the air, under the control of a central processing unit (CPU) 84, which may include a display and user controls.

Figure 5:
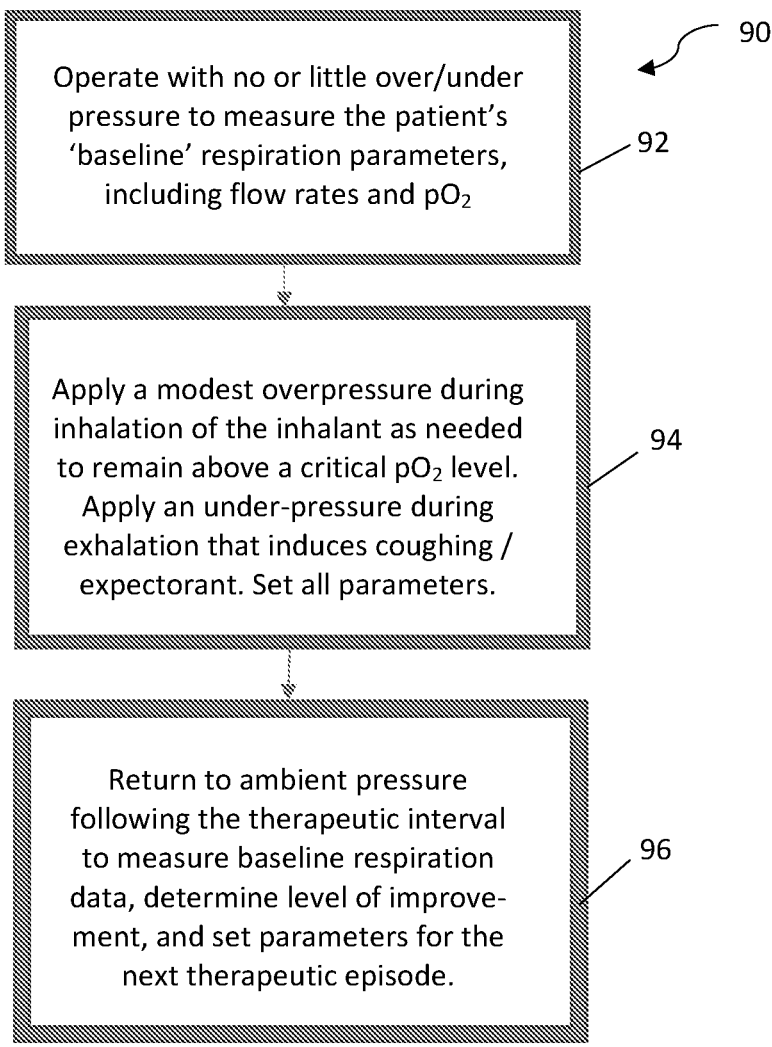
FIG. 5 is a flowchart of a method for use of the present invention.

FIG. 5 is a flowchart 90 of a method for use of the present invention. In step 92, the device of the present invention operates with no or little over/under pressure to measure the patient's 'baseline' respiration parameters, including flow rates and $pO_2$. Next, in step 94, the pressure oscillating unit apply a modest overpressure during inhalation of the inhalant as needed to remain above a critical $pO_2$ level, and then applies a sudden, large under-pressure during exhalation that may induce coughing/expectorant, at which an initial set of parameters is set. Finally, at step 96, the device returns to ambient pressure following the therapeutic interval to measure baseline respiration data, determine level of improvement, and set parameters for the next therapeutic episode.

Thus, in certain aspects, the present invention includes a device that can deliver adaptive positive and negative pressures, relative to ambient pressure, of a duration that may be set either externally, or allowed to adapt to the natural breathing rhythm of the patient. The device can also include an integrated capability to measure the air flow into and out of the patient during breathing.

A device with an integrated capability to adjust the oxygen partial pressure, and the amount of an aerosolized drug cocktail that is mixed with air to form the inhalant that is delivered to the patient to breathe. The device can also include an integrated capability to deliver ultrasound directed down the airway over a range of frequencies and intensities that are either set manually by a care provider or set automatically through an automated system. The device can also include an integrated capability to vary all of the parameters mentioned above (the duration and degree of overpressure and under-pressure applied during the patient's breathing sequence, the frequency of therapeutic bursts (described above), the frequency and intensity of ultrasound levels, the ratio of oxygen partial pressure mixed with air, and the dose of aerosolized drug delivery that is added to the inhalant) either by 1) a care provider, or 2) by a pre-programmed sequence, or 3) adaptively by an expert system that designed to adjust this parameter to increase the level of inhalant flow into and out of the lungs, and to increase the $pO_2$ indication from the patient. The device can also include an integrated capability to operate in either a normal mode that senses and adapts to the patient's normal respiration cycles, or that operates in a burst mode to break up the deep mucus on the alveoli The device can also include an integrated capability to attach to commercially available intubation tubes that have been used to intubate the patient, and hence to more effectively apply the device's therapeutic sequences (described above) down the airway. The device can also include integrated capability to detect coughing and other indicators of respiratory reflex and distress. The device can also include integrated capability to detect, remove, and contain sputum and other vile, virus-laden expectorants as it operates. The device can also include integrated capability to provide vital information, including but not limited to natural breathing rates, inhalant flow rates and its time profile while the patient breathes, and history efficacy of the parameters used in therapeutic bursts, to a device that records the time history of the patient's vital statistics and medical record data.

The device can also be readily mass-produced using components provided by original-equipment manufactures to supply the CPAP medical device industry. The device can be applied to a broad range of patient conditions arising from respiratory infections, such as COVID-19, or any other condition, such as generalized pneumonia conditions from any origin, some pneumothorax conditions, and in the recovery from drowning, or the inhalation of high molecular-weight or toxic vapors.

Figure 6:
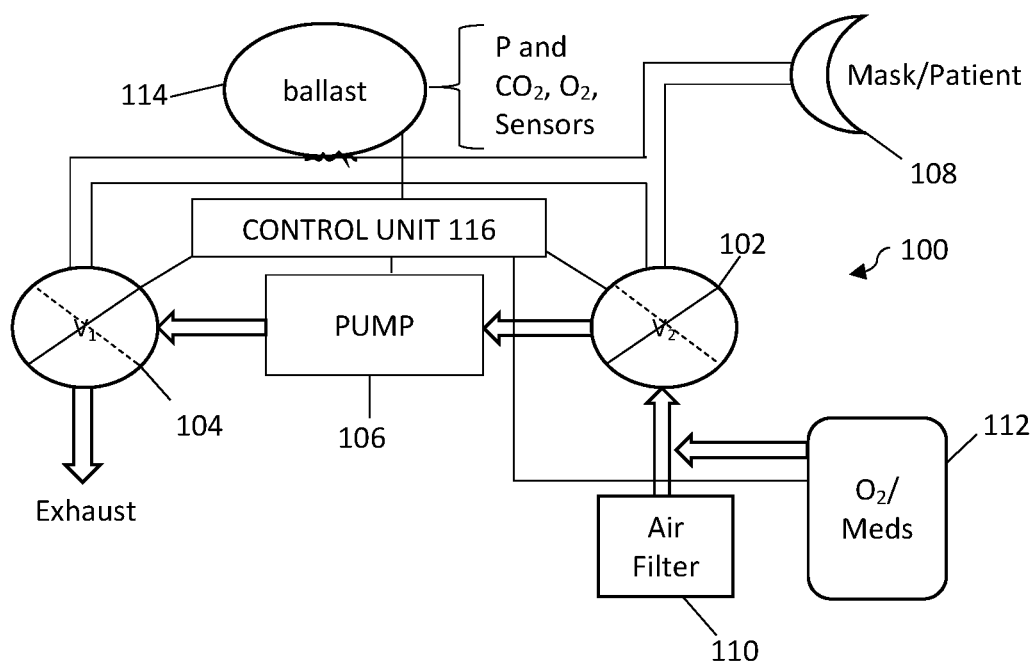
FIG. 6 shows another embodiment of an apparatus of the present invention.

FIG. 6 shows another embodiment of an apparatus of the present invention. In this apparatus 100, a first and a second valve ($V_1$) 102 and ($V_2$) 104, respectively, are flow valves are connected to a pump 106, which provides a flow of about 45-55 L/min, but often 50 L/min, in which each valve 102, 104 switches each half-cycle of respiration. As shown, the valves ($V_1$, $V_2$)(102, 104) pull a vacuum using the pump 100 connected to a mask 108 to assist with exhale. The pump output is exhausted from $V_1$ 104. After switching, the pump inlet is supplied with filtered air ($O_2$) from air filter 110 and/or $O_2$/medication from reservoir 112 as specified, and the outlet provides this mix compressed to the mask 108. This value state is shown in the dashed line in the 2-state valve diagram. A ballast 114 is connected between the valves ($V_1$, $V_2$)(102, 104), and the ballast volume provides a pressure P, and may also contain sensors for safety and control, which can include a pressure sensor, to detect change in respiration from inhale to exhale, and possible $O_2/CO_2$ partial pressure sensors. A control unit 116 is connected to the pump 106, first and second valves 102, 104, the ballast/sensors 114, reservoir 112 to control the timing and operation of the apparatus 100.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element (s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

[1] Q. Liu, R. Wang, G. Qu et al., Gross examination report of a COVID-19 death autopsy, Journal of forensic medicine, 2020, 36(1): 19-21. In Chinese.
[2] Z. Xu, L. Shi, Y. Wang, et al., Pathological findings of COVID-19 associated with acute respiratory distress syndrome[J]. Lancet Respir Med, 2020, In press, https://doi.org/10.1016/S2213-2600(20)30076-X

What is claimed is:

1. A respiratory device capable of breaking up mucus in a lung comprising:
   a chamber having an inlet and an outlet;
   a pressure oscillating unit in fluid communication with the chamber for supplying and vacuuming air into/out of the chamber, wherein the pressure oscillating unit creates ultrasonic waves;
   a control unit for selecting a positive air pressure or a negative air pressure from the pressure oscillating unit,
   a fluid container in fluid communication with the chamber;
   a pressure sensor in fluid communication with the chamber; and
   an outlet connected to the chamber to send respiration gas to a patient, ultrasonic waves in the respiration gas are capable of breaking up mucus in the lung,
   wherein the control unit is configured to modulate an over-pressure of up to 10 cm of $H_2O$ during an inhalation of the patient, and then goes to an under-pressure of −10 to −30 cm of $H_2O$ to force an exhalation much more rapid than the inhalation; and
   wherein the control unit adjusts one or more parameters selected from: a duration and a degree of overpressure and under-pressure applied during a patient's breathing sequence and a frequency and intensity of ultrasound levels, wherein each can be adjusted (1) manually, (2) automatically by a pre-programmed sequence, or (3) adaptively by a code segment that adjusts the one or more parameter to: increase a level of inhalant flow into and out of the lungs, to increase the $pO_2$ indication from the patient, or both.

2. The device of claim 1, further comprising a sensor in communication with the outlet of the chamber that measures an air flow into and out of the patient during breathing.

3. The device of claim 1, wherein the chamber is defined further as a mask capable of a substantially hermetic seal with a patient.

4. The device of claim 1, further comprising a port in fluid communication with the chamber wherein an aerosolized drug can be injected into the chamber via the port.

5. The device of claim 1, wherein at least one of:
   the control unit adjusts an oxygen partial pressure, and an amount of an aerosolized drug cocktail that is mixed with air to form an inhalant that is delivered to the lung;
   the control unit adjusts the ultrasonic waves into the outlet over a range of frequencies and intensities that are either set manually or set automatically through an automated system;
   the control unit adjusts one or more parameters selected from: a frequency of therapeutic bursts, a ratio of oxygen partial pressure mixed with air, and a dose of aerosolized drug delivery that is added to the inhalant, wherein each can be adjusted (1) manually, (2) automatically by a pre-programmed sequence, or (3) adaptively by a code segment that adjusts the one or more parameter to: increase a level of inhalant flow into and out of the lungs, to increase the $pO_2$ indication from the patient, or both;
   the control unit operates in a normal mode that senses and adapts to a patient's normal respiration cycles, or that operates in a burst mode to break up the deep mucus on the alveoli;
   the control unit detects coughing and other indicators of respiratory reflex and distress;

the control unit is connected to a display or output that provides vital information selected from at least one of: natural breathing rates, inhalant flow rates a time profile while a patient breathes, a history efficacy of one or more parameters used in therapeutic bursts, a device that records a time history of a patient's vital statistics and medical record data;

the control unit detects sputum or other fluids, a valve opens to remove and contain the sputum or other secreted fluids, wherein the sputum or other fluids comprise bacterial, fungal, or virus-laden expectorants; or the control unit adjusts one or more parameters for respiratory infections, generalized pneumonia conditions, pneumothorax conditions, drowning, or inhalation of high molecular-weight or toxic vapors.

6. The device of claim 1, wherein the pressure oscillating unit generates a large amplitude, negative pressure swing to force rapid exhalation.

7. The device of claim 1, wherein the device attaches to one or more intubation tubes and the controller applies one or more therapeutic sequences down an airway through the intubation tubes; or the device attaches to a modified continuous positive airway pressure (CPAP) medical device to produce sudden swings to negative pressure.

8. The device of claim 1, wherein the chamber is connected to an intubation tube capable of direct connection to a lung damaged by a virus.

* * * * *